United States Patent [19]

Obata et al.

[11] Patent Number: 5,369,116

[45] Date of Patent: Nov. 29, 1994

[54] POLYFLUORINATED THIAZOLINE DERIVATIVE AND CHEMICAL FOR CONTROLLING NOXIOUS ORGANISMS CONTAINING THE SAME

[75] Inventors: Tokio Obata; Katsutoshi Fujii; Yasuhisa Fukuda, Kiyashi Tsutsumiuchi, Yoshinori Yamanaka, all of Ube, Japan

[73] Assignee: Ube Industries, Ltd., Yamaguchi, Japan

[21] Appl. No.: 85,060

[22] Filed: Jul. 2, 1993

[30] Foreign Application Priority Data

Jul. 3, 1992 [JP] Japan ................................ 4-214447

[51] Int. Cl.$^5$ .................... C07D 277/42; A01N 43/78
[52] U.S. Cl. .................................. 514/370; 514/342; 546/280; 548/190; 548/195
[58] Field of Search .............. 548/190, 195; 546/280; 514/370, 342

[56] References Cited

U.S. PATENT DOCUMENTS 4,249,012  2/1981  Crossley ........................ 548/195
5,221,685  6/1993  Obata ............................. 514/371

Primary Examiner—Robert Gerstl
Attorney, Agent, or Firm—Finnegan, Henderson, Farabow, Garrett & Dunner

[57] ABSTRACT

Disclosed are a polyfluorinated thiazoline compound represented by the following formula (I):

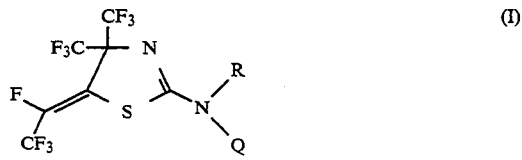

wherein
Q represents a phenyl group; a phenyl group substituted by a halogen atom, a halo-lower alkyl group, a nitro group, a cyano group, a formyl group, a lower alkoxycarbonyl group or a benzoyl group; a pyridyl group; or a pyridyl group substituted by a halogen atom, a halo-lower alkyl group, a nitro group, a cyano group, a formyl group, a lower alkoxycarbonyl group or a benzoyl group; and
R represents a hydrogen atom, a lower alkyl group or an acetyl group, and a chemical for controlling noxious organisms containing the same as an active ingredient.

8 Claims, No Drawings

POLYFLUORINATED THIAZOLINE DERIVATIVE AND CHEMICAL FOR CONTROLLING NOXIOUS ORGANISMS CONTAINING THE SAME

BACKGROUND OF THE INVENTION

This invention relates to a novel polyfluorinated thiazoline derivative which is available as a chemical for controlling noxious organisms, such as a fungicide, acaricide and insecticide.

As a similar compound in structure to a thiazoline derivative of the present invention, 2-acetamido-4,4-bis(trifluoromethyl)-5-tetrafluoroethylidene)-thiazoline has been described in Japanese Provisional Patent Publication No. 57371/1985. However, in the above publication, there is no description about the use as an agricultural agent or biological test of the compound. Also, EP-A-0 497 367 (which corresponds to U.S. Ser. No. 07/828,110 now received a Notice of Allowance) which was published after the priority date of this case discloses a thiazoline derivative but a substituent thereof is different from the present invention.

The polyfluorinated thiazoline derivatives of the present invention are novel compounds, and thus their activities of controlling noxious organisms have been not known.

SUMMARY OF THE INVENTION

An object of the present invention is to provide a novel polyfluorinated thiazoline, a process for preparing the same and a chemical for controlling noxious organisms containing the same as an effective ingredient.

The present inventors have studied intensively in order to solve the above problems, and consequently found that a novel thiazoline derivative has remarkable activity of controlling noxious organisms, to accomplish the present invention.

That is, the present invention is concerned to a polyfluorinated thiazoline derivative represented by the following formula (I):

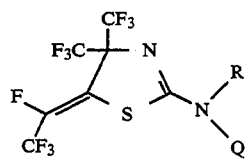
(I)

wherein

Q represents a phenyl group; a phenyl group substituted by a halogen atom, a halo-lower alkyl group, a nitro group, a cyano group, a formyl group, a lower alkoxycarbonyl group or a benzoyl group; a pyridyl group; or a pyridyl group substituted by a halogen atom, a halo-lower alkyl group, a nitro group, a cyano group, a formyl group, a lower alkoxycarbonyl group or a benzoyl group; and R represents a hydrogen atom, a lower alkyl group or an acetyl group.

The second invention relates to a process for preparing a polyfluorinated thiazoline derivative represented by the formula (I-1):

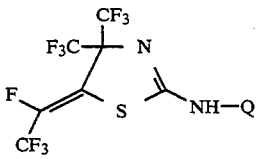
(I-1)

wherein

Q has the same meaning as defined above, among the compound represented by the above formula (I) which comprises reacting a 2-amino-2-thiazoline derivative represented by the following formula (II):

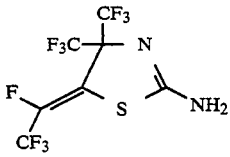
(II)

with a compound represented by the following formula (III):

X—Q   (III)

wherein

Q has the same meaning as defined above and

X represents an eliminatable group.

The third invention relates to a process for preparing a polyfluorinated thiazoline derivative represented by the following formula (I-2):

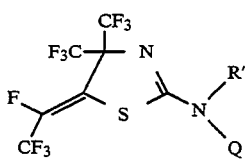
(I-2)

wherein

Q has the same meaning as defined above, and

R' represents a lower alkyl group or an acetyl group, among the compound represented by the above formula (I) which comprises reacting the polyfluorinated thiazoline derivative represented by the above formula (I-1) and a compound represented by the following formula (IV):

Y—R   (IV)

wherein

R' has the same meaning as defined above, and

Y represents an eliminatable group.

The fourth invention relates to a chemical for controlling noxious organisms containing the polyfluorinated thiazoline derivative represented by the above formula (I) as an effective ingredient.

DESCRIPTION OF THE PREFERRED EMBODIMENTS

In the following, the present invention will be explained in detail.

In the novel polyfluorinated thiazoline derivative (I) of the present invention including compounds of the formulae (I-1) and (I-2) as well as the starting materials thereof (Compounds of the formulae (III) and (IV)), the respective substituents Q, R, R', X and Y are as follows.

As the substituent Q, there may be mentioned a substituted or unsubstituted phenyl group and a substituted or unsubstituted pyridyl group.

The substituents for the phenyl group and the pyridyl group in the substituent Q may include, for example, a halogen atom, a halo-lower alkyl group, a nitro group, a cyano group, a benzoyl group, a formyl group and a lower alkoxycarbonyl group; and, as the substituent for the pyridyl group, a halogen atom, a halo-lower alkyl group and a nitro group are preferred.

As the halogen atom which is a substituent for the phenyl group or the pyridyl group of Q, there may be mentioned, for example, a chlorine atom, an iodine atom, a bromine atom and a fluorine atom; preferably a chlorine atom and a fluorine atom; more preferably a chlorine atom for the pyridyl group.

As the halo-lower alkyl group which is a substituent for the phenyl group or the pyridyl group of Q, there may be mentioned, for example, a straight or branched alkyl group with 1 to 6 carbon atoms and having a halogen atom (e.g. chlorine atom, iodine atom, bromine atom and fluorine atom); preferably a straight or branched one with 1 to 4 carbon atoms; more preferably trifluoromethyl group.

As the alkoxy moiety of the lower alkoxycarbonyl group which is a substituent for the phenyl group or the pyridyl group of Q, there may be mentioned, for example, those having a straight or branched alkoxy moiety with 1 to 6 carbon atoms; preferably those having a straight or branched alkoxy moiety with 1 to 4 carbon atoms; more preferably a methoxycarbonyl group. As the Q having most preferred alkoxycarbonyl group, there may be mentioned a phenyl group having a methoxycarbonyl group.

As the number of the substituent(s) for the phenyl group or the pyridyl group in the Q, it may be 0 to 5; and preferably 1 to 5

Preferred examples of the Q may include a phenyl group, a 2,6-dichloro-4-trifluoromethylphenyl group, a 2-nitro-4-trifluoromethylphenyl group, a 2,4-dinitro-6-trifluoromethylphenyl group, a 2,6-dinitro-4-trifluoromethylphenyl group, a 4-cyano-2,6-dinitrophenyl group, a 3-chloro-2,6-dinitro-4-trifluoromethylphenyl group, a 4-nitro-3-trifluoromethylphenyl group, a 3,4-dichloro-2-nitrophenyl group, a 4-cyano-2,3,5,6-tetrafluorophenyl group, a 5-chloro-2-nitro-4-trifluoromethylphenyl group, a 2-chloro-6-nitro-4-trifluoromethylphenyl group, a 2-chloro-4-nitro-5-trifluoromethylphenyl group, a 4-fluorophenyl group, a 5-flouro- 2-nitro-4-trifluoromethylphenyl group, a 2,4-dinitrophenyl group, a 4-nitro-2-trifluoromethylphenyl group, a 4-benzoyl-2-nitrophenyl group, a 2-cyano-4-nitrophenyl group, a 2-formyl-4-nitrophenyl group, a 5-chloro-2-nitrophenyl group, a 5-chloro-2-methoxycarbonylphenyl group, a 4-chloro-2-nitrophenyl group, a 2-chloro-6-nitrophenyl group, a 2-chloro-4-nitrophenyl group, a 2,4,6-trinitrophenyl group, a 4-nitrophenyl group, a 2,4-bis(trifluoromethyl)phenyl group, a 2-chloro-4-trifluoromethylphenyl group, a 4-trifluoromethylphenyl group, a 2-trifluoromethyl group, a 2-nitrophenyl group; a pyridyl group, a 3-chloro-5-trifluoromethyl-2-pyridyl group, a 6-chloro-4-trifluoromethyl-2-pyridyl group, a 5-trifluoromethyl-2-pyridyl group, a 5-nitro-2-pyridyl group, a 3-trifluoromethyl-2-pyridyl group, a 3,5-dinitro-2-pyridyl group, and the like.

Among these, particularly preferred are a 2,6-dichloro-4-trifluoromethylphenyl group, a 2-nitro-4-trifluoromethylphenyl group, a 2,4-dinitro-6-trifluoromethylphenyl group, a 2,6-dinitro-4-trifluoromethylphenyl group, a 4-cyano-2,6-dinitrophenyl group, a 4-nitro-3-trifluoromethylphenyl group, a 3,4-dichloro-2-nitrophenyl group, a 4-cyano-2,3,5,6-tetrafluorophenyl group, a 2-chloro-4-nitro-5-trifluoromethylphenyl group, a 5-fluoro-2-nitro-4-trifluoromethylphenyl group, a 2,4-dinitrophenyl group, a 4-nitro-2-trifluoromethylphenyl group, a pyridyl group, a 3-chloro-5-trifluoromethyl-2-pyridyl group, a 6-chloro-4-trifluoromethyl-2-pyridyl group and a 3,5-dinitro-2-pyridyl group.

As the R, there may be mentioned a hydrogen atom, a lower alkyl group and an acetyl group.

As the lower alkyl group of the R, there may be mentioned a straight or branched one with 1 to 6 carbon atoms; preferably a straight or branched one with 1 to 4 carbon atoms; more preferably a methyl group.

As the R', there may be mentioned a lower alkyl group and an acetyl group.

As the lower alkyl group of the R', there may be mentioned a straight or branched one with 1 to 6 carbon atoms; preferably a straight or branched one with 1 to 4 carbon atoms; more preferably a methyl group.

As an eliminatable group X in the starting compound (III) and an eliminatable group Y in the starting compound (IV) for preparing the compound (I) of the present invention, they are not specifically limited.

As the eliminatable group X, there may be mentioned, for example, a usual eliminatable group in the aromatic nucleophilic substitution reaction such as a halogen group (a chlorine atom, a fluorine atom, a bromine atom and an iodine atom), an alkanesulfonyl group (a methanesulfonyl group and an ethanesulfonyl group), an alkanesulfinyl group (a methanesulfinyl group and an ethanesulfinyl group), an arylsulfonyl group (a benzenesulfonyl group and a p-toluenesulfonyl group), an arylsulfinyl group (a benzenesulfinyl group and a p-toluenesulfinyl group), a nitro group and a diazo group. Preferable eliminatable group X includes a halogen atom (a chlorine atom, a fluorine atom, a bromine atom and an iodine atom) and an alkanesulfonyl group; more preferably a fluorine atom, a chlorine atom and a methanesulfonyl group.

As the eliminatable group Y, when R' is a lower alkyl group, there may be preferably mentioned a halogen group (a chlorine atom, a fluorine atom, a bromine atom and an iodine atom), an alkanesulfoxy group (in Y—R', those generally forming dialkylsulfate), an arylsulfoxy group (e.g. a benzenesulfoxy group, a p-toluenesulfoxy group); more preferably an iodine atom; and when R' is an acetyl group, there may be preferably mentioned a halogen group (a chlorine atom, a fluorine atom, a bromine atom and an iodine atom) and an acetoxy group.

The compound (I) of the present invention can be prepared, for example, according to the preparation methods 1 to 3 as mentioned below.

SYNTHETIC METHOD 1

Synthesis of the compound (I-1) in which R in the compound (I) is a hydrogen atom of the present invention can be generally carried out by reacting the 2-iminothiazoline derivative represented by the following formula (V):

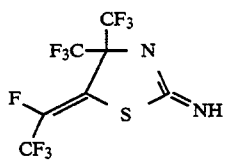 (V)

and the compound (III) in a solvent in the presence of a base.

The solvent is not particularly limited so long as it does not participate in the present reaction directly, and may include, for example, chlorinated or unchlorinated aromatic, aliphatic or alicyclic hydrocarbons such as benzene, toluene, xylene, methylnaphthalene, petroleum ether, ligroin, hexane, chlorobenzene, dichlorobenzene, chloroform, dichloromethane, dichloroethane, trichloroethylene and cyclohexane; ethers such as diethyl ether, tetrahydrofuran and dioxane; ketones such as acetone and methyl ethyl ketone; amides such as N,N-dimethylformamide and N,N-dimethylacetamide; organic bases such as triethylamine, pyridine and N,N-dimethylaniline; 1,3-dimethyl-2-imidazolidinone; dimethyl sulfoxide; and a mixture of the above solvents.

The solvent may be used such an amount that a concentration of the compound (V) is in the range of 5 to 80% by weight, but preferably such an amount that the concentration of the compound (V) is in the range of 10 to 70% by weight.

As the base, there may be mentioned an organic base such as triethylamine, pyridine, 4-(N,N-dimethylamino)pyridine and N,N-dimethylaniline; and an inorganic base such as sodium amide, sodium hydroxide, potassium hydroxide, potassium carbonate, sodium carbonate and sodium hydride, and the like.

The base may be used in an amount of 0.001 to 5-fold mole per mole of the compound (V).

The reaction temperature is not particularly limited, but it is generally carried out in the temperature range of from room temperature to a boiling point or lower of a solvent used, and preferably under heating in the temperature range of the boiling point or lower.

The reaction time varies depending on the above concentration of the starting materials and the temperature, but may be generally 0.3 to 24 hours.

The starting compound (III) may be used in an amount of 0.5 to 2-fold mole based on the mole of the starting compound (V), but preferably 0.8 to 1.5-fold mole.

The compound (V) to be used in the present invention can be easily produced, for example, by using perfluoro-(2-methyl-2-pentene), etc. and thiourea according to the method described in Japanese Provisional Patent Publication No. 57371/1983, etc.

Among the compound (III) to be used in the present invention, those which cannot be commercially available can be produced according to the method known in the art by a literature, etc. For example, in the case of halonitrobenzene derivatives, they can be produced by nitrating a corresponding halobenzene according to the method described in Japanese Patent Publication No. 42061/1980.

As the compound (III), there may be mentioned, for example, each compound (III) (referred to as Compound (III)$_1$ to (III)$_{39}$) comprising respective kinds of substituents corresponding to Compounds No. 1 to 39 shown in Table 1 below (for example, compound (III) corresponding to Compound No. 1 is referred to as Compound (III)$_1$. Compound (III)$_1$ is a compound wherein Q in the formula (III) is 3-chloro-5-trifluoromethyl-2-pyridyl group.).

SYNTHETIC METHOD 2

Synthesis of the compound (I-1) in which R in the compound (I) of the present invention is a hydrogen atom can be carried out in the same manner as in Synthetic method 1 except for using a compound (II) in place of the starting compound (V).

The compound (II) to be used in the present invention can be synthesized by isomerizing the compound (V) in sulfuric acid in accordance with the method as described in Japanese Provisional Patent Publication No. 57371/1983, etc.

SYNTHETIC METHOD 3

Synthesis of the compound (I-2) in which R in the compound (I) of the present invention is a lower alkyl group or an acetyl group can be carried out by reacting the compound (I-1) with the compound (IV) in a solvent in the presence of a base.

The solvent is not particularly limited so long as it does not participate in the present reaction directly, and may include, for example, chlorinated or unchlorinated aromatic, aliphatic or alicyclic hydrocarbons such as benzene, toluene, xylene, methylnaphthalene, petroleum ether, ligroin, hexane, chlorobenzene, dichlorobenzene, chloroform, dichloromethane, dichloroethane, trichloroethylene and cyclohexane; ethers such as diethyl ether, tetrahydrofuran and dioxane; alcohols such as methanol, ethanol and ethylene glycol or hydrates thereof; dimethyl sulfoxide; carbon disulfide; and a mixture of the above solvents.

The solvent may be used such an amount that a concentration of the compound (I-1) is in the range of 5 to 80% by weight, but preferably such an amount that the concentration of the compound (I-1) is in the range of 10 to 70% by weight.

As the base, there may be mentioned an organic base such as triethylamine, pyridine, 4-(N,N-dimethylamino)pyridine and N,N-dimethylaniline; and an inorganic base such as sodium amide, sodium hydroxide, potassium hydroxide, potassium carbonate, sodium carbonate and sodium hydride, and the like.

The reaction temperature is not particularly limited, but it is generally carried out in the temperature range of from room temperature to a boiling point or lower of a solvent used, and preferably under heating in the temperature range of the boiling point or lower.

The reaction time varies depending on the above concentration of the starting material and the temperature, but may be generally 0.3 to 24 hours.

The desired compound (I) prepared as mentioned above can be optionally purified, after completion of the reaction, by the conventional post-treatment such as extraction, condensation and filtration, and if necessary, by the known means such as recrystallization and various kinds of chromatographies.

As the compound (I), there may be mentioned, for example, Compounds No. 1 to 39 shown in Table 1 below (for example, Compound No. 1 means a compound wherein Q in the compound represented by the formula (I) is 3-chloro-5-trifluoromethyl-2-pyridyl group, and R in the same is a hydrogen atom.).

As the noxious organisms on which controlling effect by the desired compound (I) of the present invention can be observed, there may be mentioned agricultural and horticultural noxious insects (e.g. Hemiptera (e.g. planthoppers, leafhoppers, aphids and whiteflies), Lepidoptera (e.g. cabbage armyworms, diamondback moth, leafroller moths, pyralid moths and con, non cabbage worm), Coleoptera (e.g. tenebrionid beetles, leaf beetles, weevils and scarabs) and Acarina (e.g. citrus red mite and two-spotted spider mite of Tetranychidae family, and pink citrus rust mite of Eriophyidae family)), hygienically noxious insects (e.g. flies, mosquitos and cockroaches), noxious insects of stored grains, and root knot nematode, pine wood nematode and bulb mite in soil, and also agricultural and horticultural diseases (e.g. brown rust (wheat), powdery mildew (barley), downy mildew (cucumber), blast (rice) and late blight (tomato)).

The chemical for controlling noxious organisms of the present invention has remarkable insecticidal, acaricidal and fungicidal effects, and contains at least one compound (I) as an active ingredient.

The compound (I) can be used singly, but may be preferably used by mixing with a carrier, a surfactant, a dispersant and an auxiliary (for example, prepared as a composition such as a dust, an emulsion, a fine granule, a granule, a wettable powder, an aqueous or oily suspension and an aerosol) according to a conventional method.

As the carrier, there may be mentioned, for example, a solid carrier such as talc, bentonite, clay, kaolin, diatomaceous earth, white carbon, vermiculite, slaked lime, siliceous sand, ammonium sulfate and urea; a liquid carrier such as hydrocarbons (e.g. kerosine and mineral oil), aromatic hydrocarbons (e.g. benzene, toluene and xylene), chlorinated hydrocarbons (e.g. chloroform and carbon tetrachloride), ethers (e.g. dioxane and tetrahydrofuran), ketones (e.g. acetone, cyclohexanone and isophorone), esters (e.g. ethyl acetate, ethylene glycol acetate and dibutyl maleate), alcohols (e.g. methanol, n-hexanol and ethylene glycol), polar solvents (e.g. dimethylformamide and dimethylsulfoxide) and water; and a gas carrier such as air, nitrogen, carbon dioxide and freon (in the case of a gas carrier, mixed spray can be carried out).

As the surfactant and dispersant which can be used for improving attachment of the present chemical to and absorption thereof in animals and plants, and improving characteristics such as dispersion, emulsification and spreading of the chemical, there may be mentioned, for example, alcohol sulfates, alkylsulfonate, lignin sulfonate and polyoxyethylene glycol ether. Further, for improving properties of its preparation, for example, carboxymethyl cellulose, polyethylene glycol and gum arabic can be used as an auxiliary.

In preparation of the present chemical, the above carrier, surfactant, dispersant and auxiliary can be used singly or in a suitable combination, respectively, depending on the respective purposes.

When the compound (I) of the present invention is made into preparations, the concentration of the active ingredient is generally 1 to 50% by weight in an emulsion, generally 0.3 to 25% by weight in a dust, generally 1 to 90% by weight in a wettable powder, generally 0.5 to 5% by weight in a granule, generally 0.5 to 5% by weight in an oily dispersion, and generally 0.1 to 5% by weight in an aerosol.

These medical preparations can be provided for various uses by diluting them to have a suitable concentration and spraying them to stems and leaves of plants, soil and paddy field surface, or by applying them directly thereto, depending on the purposes.

EXAMPLES

The present invention is described in detail by referring to Reference example and Examples, but the scope of the present invention is not limited by these examples.

EXAMPLE 1

Synthesis of Compound (I) According to Synthetic Method 1

(1) Synthesis of 2-[(3-chloro-2,6-dinitro-4-trifluoromethylphenyl)amino]-4,4-bis(trifluoromethyl)-5-tetrafluoroethylidene)-2-thiazoline (Compound No. 12)

In 20 ml of N,N-dimethylacetamide were suspended 3 g of 2-imino-4,4-bis(trifluoromethyl)-5-(tetrafluoroethylidene)-1,3-thiazolidine, 3 g of 2,4-dichloro-3,5-dinitrobenzotrifluoride and 2 g of potassium carbonate, and the suspension was stirred at 70° to 80° C. for 4 hours.

After the reaction, the reaction mixture was neutralized with 1N hydrochloric acid and extracted with toluene, and the extract was washed with water. After the extract was dried over anhydrous sodium sulfate, the solvent was removed under reduced pressure.

The resulting oily product was purified by column chromatography (Wako gel C-200 (trade name, produced by Wako Junyaku K.K.), eluted by toluene:ethyl acetate=30:1) to obtain 0.2 g of the title compound (I) as pale yellow crystals.

EXAMPLE 2

Synthesis of Compound (I) According to Synthetic Method 2 or 3

(1) Synthesis of 2-[(3-chloro-5-trifluoromethyl-2pyridyl)amino]-4,4-bis(trifluoromethyl)-5-(tetrafluoroethylidene)-2-thiazoline (Compound No. 1)

According to Synthetic method 2, Compound No. 1 was synthesized as follows.

In 10 ml of N,N-dimethylacetamide were suspended 1 g of 2-imino-4,4-bis(trifluoromethyl)-5-(tetrafluoroethylidene)-2-thiazolidine, 0.7 g of 2,3-dichloro-5-trifluoromethylpyridine and 0.4 g of potassium carbonate, and the suspension was stirred at 60° to 70° C. for 3 hours.

After the reaction, the reaction mixture was extracted with toluene, the extract was washed with water and dried over anhydrous sodium sulfate, and then the solvent was removed under reduced pressure.

The resulting oily product was purified by column chromatography (Wako gel C-200 (trade name, produced by Wako Junyaku K.K.), eluted by toluene:ethyl acetate=20:1) to obtain 0.2 g of the title compound (I) as colorless crystals.

(2) Synthesis of 2-[(2,6-dinitro-4-cyanophenyl)amino]-4,4-bis(trifluoromethyl)-5-(tetrafluoroethylidene)-2-thiazoline (Compound No. 9)

According to Synthetic method 2, Compound 9 was synthesized as follows.

In 10 ml of N,N-dimethylacetamide were suspended 1 g of 2-amino-4,4-bis(trifluoromethyl)-5-(tetrafluoroethylidene)-2-thiazoline, 0.8 g of 4-chloro-3,5-dinitrobenzonitrile and 1 g of potassium carbonate, and the suspension was stirred at 70° to 80° C. for 8 hours.

After the reaction, the reaction mixture was neutralized with 1N hydrochloric acid and extracted with toluene, and the extract was washed with water. After the extract was dried over anhydrous sodium sulfate, the solvent was removed under reduced pressure.

The resulting oily product was purified by column chromatography (Wako gel C-200 (trade name, produced by Wako Junyaku K.K.), eluted by toluene:ethyl acetate=10:1) to obtain 0.8 g of the title compound (I) as yellow crystals.

(3) Synthesis of 2-[(4-nitro-2-trifluoromethylphenyl)amino]-4,4-bis(trifluoromethyl)-5-(tetrafluoroethylidene)-2-thiazoline (Compound No. 23)

According to Synthetic method 2, Compound No. 23 was synthesized as follows.

In 10 ml of N, N-dimethylacetamide were suspended 0.8 g of 2-amino-4,4-bis(trifluoromethyl)-5-(tetrafluoroethylidene)- 2-thiazolidine, 0.65 g of 2-chloro-5-nitrobenzotrifluoride and 0.5 g of potassium carbonate, and the suspension was stirred at 80° to 90° C. for 8 hours.

After the reaction, the reaction mixture was neutralized with 1N hydrochloric acid and extracted with toluene, and the extract was washed with water. After the extract was dried over anhydrous sodium sulfate, the solvent was removed under reduced pressure.

The resulting oily product was purified by column chromatography (Wako gel C-200 (trade name, produced by Wako Junyaku K.K.), eluted by toluene:ethyl acetate=10:1) to obtain 0.7 g of the title compound (I) as yellow crystals.

(4) Synthesis of 2-[[2,4-bis(trifluoromethyl)phenyl]amino]-4,4-bis(trifluoromethyl)-5-(tetrafluoroethylidene)-2-thiazoline (Compound No. 35)

According to Synthetic method 2, Compound No. 35 was synthesized as follows.

In 5 ml of N,N-dimethylacetamide were suspended 0.65 g of 2-amino-4,4-bis(trifluoromethyl)-5-(tetrafluoroethylidene)-2-thiazolidine, 0.6 g of 2,4-bis(trifluoromethyl)methanesulfonylbenzene and 0.55 g of potassium carbonate, and the suspension was stirred at 80° to 90° C. for 8 hours.

After the reaction, the reaction mixture was neutralized with 1N hydrochloric acid and extracted with toluene, and the extract was washed with water. After the extract was dried over anhydrous sodium sulfate, the solvent was removed under reduced pressure.

The resulting oily product was purified by column chromatography (Wako gel C-200 (trade name, produced by Wako Junyaku K.K.), eluted by hexane:toluene=1:1) to obtain 0.26 g of the title compound (I) as colorless crystals.

(5) Synthesis of 2-[N-methyl-N-(2,6-dinitro-4-trifluoromethylphenyl)amino]-4,4-bis(trifluoromethyl)-5-(tetrafluoroethylidene)-2-thiazoline (Compound No. 11)

According to Synthetic method 3, Compound No. 11 was synthesized as follows.

In 5 ml of N,N-dimethylformamide were suspended 0.15 g of 2-[(2,6-dinitro-4-trifluoromethylphenyl)amino]-4,4-bis(trifluoromethyl)-5-(tetrafluoroethylidene)-2-thiazoline and 0.2 g of potassium carbonate, and 0.2 g of methyl iodide was added to the suspension. Then, the mixture was stirred at 40° to 50° C. for 4 hours.

After the reaction, the reaction mixture was neutralized with 1N hydrochloric acid and extracted with toluene, the extract was washed with water, dried over anhydrous sodium sulfate, and the solvent was removed under reduced pressure.

The resulting oily product was purified by column chromatography (Wako gel C-200 (trade name, produced by Wako Junyaku K.K.), eluted by toluene:ethyl acetate=30:1) to obtain 0.06 g of the title compound (I) as pale yellow crystals.

(6) Synthesis of Compound No. 12 and other compounds in Table 1

According to the method in the above (1) to (5), Compound No. 12 and other compounds shown in Table 1 were synthesized.

TABLE 1

(I) structure: 4,4-bis(CF$_3$), 5-(=C(F)(CF$_3$)) thiazoline with 2-N(R)(Q)

| Compound No. | R | Q | Physical properties |
|---|---|---|---|
| 1 | H | 2-Cl, 4-CF$_3$ pyridin-5-yl | m.p. 130~132° C. |
| 2 | H | 2,6-diCl-4-CF$_3$ phenyl | m.p. 151~155° C. |
| 3 | H | 4-CF$_3$, 6-Cl pyridin-3-yl | m.p. 103~105° C. |
| 4 | H | 4-CF$_3$ pyridin-2-yl | $n_D^{25.2}$ 1.4640 |
| 5 | H | 2-NO$_2$, 4-CF$_3$ phenyl | m.p. 82~84° C. |
| 6 | H | 4-NO$_2$ pyridin-2-yl | m.p. 223~225° C. |
| 7 | H | 2-NO$_2$, 4-NO$_2$, 6-CF$_3$ phenyl | m.p. 132~134° C. |

TABLE 1-continued (I) Structure: (CF3)(F3C)C-C(F)=C(CF3)-S-C(=N-R)-N(R)(Q) ... with R and Q as substituents

| Compound No. | R | Q | Physical properties |
|---|---|---|---|
| 8 | H | 2,4-(O₂N)₂-5-CF₃-phenyl | m.p. 173~175° C. |
| 9 | H | 2,4-(O₂N)₂-5-CN-phenyl | m.p. 237~239° C. |
| 10 | H | 3-CF₃-pyridin-2-yl | m.p. 90~92° C. |
| 11 | CH₃ | 2,4-(O₂N)₂-5-CF₃-phenyl | m.p. 110~113° C. |
| 12 | H | 2,4-(O₂N)₂-3-Cl-5-CF₃-phenyl | m.p. 129~131° C. |
| 13 | H | 2-NO₂-4-CF₃-phenyl | m.p. 119~121° C. |
| 14 | H | 2,3-Cl₂-5-NO₂-phenyl | m.p. 194~195° C. |
| 15 | H | 2,3,5,6-F₄-4-CN-phenyl | m.p. 179~182° C. |
| 16 | H | 2-Cl-4-NO₂-5-CF₃-phenyl | m.p. 116~119° C. |
| 17 | H | 2-Cl-4-NO₂-5-CF₃-phenyl (isomer) | — |
| 18 | H | 2-CF₃-3-NO₂-5-Cl-phenyl | — |
| 19 | H | 4-F-phenyl | m.p. 162~164° C. |
| 20 | CH₃CO | 2,4-(O₂N)₂-5-CN-phenyl | m.p. 217~223° C. |
| 21 | H | 2-F-3-CF₃-5-NO₂-phenyl | m.p. 84~86° C. |
| 22 | H | 3,4-(NO₂)₂-phenyl | m.p. 104~106° C. |
| 23 | H | 3-CF₃-4-NO₂-phenyl | m.p. 126~128° C. |

TABLE 1-continued (I) Structure with CF3, F3C, N, R, S, Q, F, CF3

| Compound No. | R | Q | Physical properties |
|---|---|---|---|
| 24 | H | 2-methyl-3,5-dinitropyridyl | m.p. 122~124° C. |
| 25 | H | 4-methyl-3-nitrophenyl benzoyl (CO-phenyl) | m.p. 162~164° C. |
| 26 | H | 2-methyl-3-cyano-5-nitrophenyl | m.p. 156~159° C. |
| 27 | H | 2-methyl-3-formyl-5-nitrophenyl | m.p. 144~146° C. |
| 28 | H | 2-methyl-4-chloro-5-nitrophenyl | m.p. 102~104° C. |
| 29 | H | 2-methyl-4-chloro-5-(methoxycarbonyl)phenyl | m.p. 124~126° C. |
| 30 | H | 2-methyl-4-chloro-5-nitrophenyl | m.p. 126~128° C. |
| 31 | H | 2-methyl-3-chloro-5-nitrophenyl | m.p. 146~149° C. |
| 32 | H | 2-methyl-3-chloro-5-nitrophenyl | m.p. 187~189° C. |
| 33 | H | 2-methyl-3,5-dinitrophenyl | m.p. 179~181° C. |
| 34 | H | 4-nitrophenyl | m.p. 173~174° C. |
| 35 | H | 3,5-bis(trifluoromethyl)phenyl | m.p. 81~83° C. |
| 36 | H | 3-chloro-5-trifluoromethylphenyl | |
| 37 | H | 4-trifluoromethylphenyl | |
| 38 | H | 3-trifluoromethylphenyl | |
| 39 | H | 3-nitrophenyl | |

In the above exemplary compounds, preferred are as shown below:

2-[(3-chloro-5-trifluoromethyl-2-pyridyl)amino]-4,4-bis(trifluoromethyl)-5-(tetrafluoroethylidene)-2-thiazoline (Compound No. 1)

2-[(2,6-dichloro-4-trifluoromethylphenyl)amino]-4,4-bis(trifluoromethyl)-5-(tetrafluoroethylidene)-2-thiazoline (Compound No. 2)

2-[(6-chloro-4-trifluoromethyl-2-pyridyl)amino]-4,4-bis(trifluoromethyl)-5-(tetrafluoroethylidene)-2-thiazoline (Compound No. 3)

2-[(5-trifluoromethyl-2-pyridyl)amino]-4,4-bis(trifluoromethyl)-5-(tetrafluoroethylidene)-2-thiazoline (Compound No. 4)

2-[(2-nitro-4-trifluoromethylphenyl)amino]-4,4-bis(trifluoromethyl)-5-(tetrafluoroethylidene)-2-thiazoline (Compound No. 5)

2-[(5-nitro-2-pyridyl)amino]-4,4-bis(trifluoromethyl)-5-(tetrafluoroethylidene)-2-thiazoline (Compound No. 6)

2-[(2,4-dinitro-6-trifluoromethylphenyl)amino]-4,4-bis(trifluoromethyl)-5-(tetrafluoroethylidene)-2-thiazoline (Compound No. 7)

2-[(2,6-dinitro-4-trifluoromethylphenyl)amino]-4,4-bis(trifluoromethyl)-5-(tetrafluoroethylidene)-2-thiazoline (Compound No. 8)

2-[(2,6-dinitro-4-cyanophenyl)amino]-4,4-bis(trifluoromethyl)-5-(tetrafluoroethylidene)-2-thiazoline (Compound No. 9)

2-[(3-trifluoromethyl-2-pyridyl)amino]-4,4-bis(trifluoromethyl)-5-(tetrafluoroethylidene)-2-thiazoline (Compound No. 10)

2-[N-methyl-N-(2,6-dinitro-4-trifluoromethylphenyl)amino]-4,4-bis(trifluoromethyl)-5-(tetrafluoroethylidene)-2-thiazoline (Compound No. 11)

2-[(3-chloro-2,6-dinitro-4-trifluoromethylphenyl)amino]-4,4-bis(trifluoromethyl)-5-tetrafluoroethylidene)-2-thiazoline (Compound No. 12)

2-[(4-nitro-5-trifluoromethylphenyl)amino]-4,4-bis(trifluoromethyl)-5-(tetrafluoroethylidene)-2-thiazoline (Compound No. 13)

2-[(3,4-dichloro-2-nitrophenyl)amino]-4,4-bis(trifluoromethyl)-5-(tetrafluoroethylidene)-2-thiazoline (Compound No. 14)

2-[(4-cyano-2,3,5,6-tetrafluorophenyl)amino]-4,4-bis(trifluoromethyl)-5-(tetrafluoroethylidene)-2-thiazoline (Compound No. 15)

2-[(5-chloro-2-nitro-4-trifluoromethylphenyl)amino]-4,4-bis(trifluoromethyl)-5-(tetrafluoroethylidene)-2-thiazoline (Compound No. 16)

2-[(2-chloro-6-nitro-4-trifluoromethylphenyl)amino]-4,4-bis(trifluoromethyl)-5-(tetrafluoroethylidene)-2-thiazoline (Compound No. 17)

2-[(2-chloro-4-nitro-5-trifluoromethylphenyl)amino]-4,4-bis(trifluoromethyl)-5-(tetrafluoroethylidene)-2-thiazoline (Compound No. 18)

2-[(4-fluorophenyl)amino]-4,4-bis(trifluoromethyl)-5-(tetrafluoroethylidene)-2-thiazoline (Compound No. 19)

2-[N-acetyl-N-(2,6-dinitro-4-cyanophenyl)amino]-4,4-bis(trifluoromethyl)-5-(tetrafluoroethylidene)-2-thiazoline (Compound No. 20)

2-[(5-fluoro-2-nitro-4-trifluoromethylphenyl)amino]-4,4-bis(trifluoromethyl)-5-(tetrafluoroethylidene)-2-thiazoline (Compound No. 21)

2-[(2,4-dinitrophenyl)amino]-4,4-bis(trifluoromethyl)-5-(tetrafluoroethylidene)-2-thiazoline (Compound No. 22)

2-[(4-nitro-2-trifluoromethylphenyl)amino]-4,4-bis(trifluoromethyl)-5-(tetrafluoroethylidene)-2-thiazoline (Compound No. 23)

2-[(3,5-dinitro-2-pyridyl)amino]-4,4-bis(trifluoromethyl)-5-(tetrafluoroethylidene)-2-thiazoline (Compound No. 24)

2-[(4-benzoyl-2-nitrophenyl)amino]-4,4-bis(trifluoromethyl)-5-(tetrafluoroethylidene)-2-thiazoline (Compound No. 25)

2-[(2-cyano-4-nitrophenyl)amino]-4,4-bis(trifluoromethyl)-5-(tetrafluoroethylidene)-2-thiazoline (Compound No. 26)

2-[(2-formyl-4-nitrophenyl)amino]-4,4-bis(trifluoromethyl)-5-(tetrafluoroethylidene)-2-thiazoline (Compound No. 27)

2-[(5-chloro-2-nitrophenyl)amino]-4,4-bis(trifluoromethyl)-5-(tetrafluoroethylidene)-2-thiazoline (Compound No. 28)

2-[(5-chloro-2-methoxycarbonylphenyl)amino]-4,4-bis(trifluoromethyl)-5-(tetrafluoroethylidene)-2-thiazoline (Compound No. 29)

2-[(4-chloro-2-nitrophenyl)amino]-4,4-bis(trifluoromethyl)-5-(tetrafluoroethylidene)-2-thiazoline (Compound No. 30)

2-[(2-chloro-6-nitrophenyl)amino]-4,4-bis(trifluoromethyl)-5-(tetrafluoroethylidene)-2-thiazoline (Compound No. 31)

2-[(2-chloro-4-nitrophenyl)amino]-4,4-bis(trifluoromethyl)-5-(tetrafluoroethylidene)-2-thiazoline (Compound No. 32)

2-[(2,4,6-trinitrophenyl)amino]-4,4-bis(trifluoromethyl)-5-(tetrafluoroethylidene)-2-thiazoline (Compound No. 33)

2-[(4-nitrophenyl)amino]-4,4-bis(trifluoromethyl)-5-(tetrafluoroethylidene)-2-thiazoline (Compound No. 34)

2-[[2,4-bis(trifluoromethyl)phenyl]amino]-4,4-bis(trifluoromethyl)-5-(tetrafluoroethylidene)-2-thiazoline (Compound No. 35).

Of these, particularly preferred are Compounds Nos. 1, 2, 3, 5, 7, 8, 9, 12, 13, 14, 15, 18, 21, 22, 23 and 24.

EXAMPLE 3

Preparation of formulation (1) Preparation of Granule

Five (5) parts by weight of Compound No. 1 was uniformly mixed with 35 parts by weight of bentonite, 57 parts by weight of talc, 1 part by weight of Neopelex powder (trade name, produced by Kao K.K.) and 2 parts by weight of lignin sodium sulfonate, and then the mixture was kneaded with addition of a small amount of water, followed by granulation and drying, to obtain a granule.

(2) Preparation of Wettable Powder

Ten (10) parts by weight of Compound No. 1 was uniformly mixed with 70 parts by weight of kaolin, 18 parts by weight of white carbon, 1.5 parts by weight of Neopelex powder (trade name, produced by Kao K.K.) and 0.5 part by weight of Demol (trade name, produced by Kao K.K.), and then the mixture was pulverized to obtain a wettable powder.

(3) Preparation of Emulsion

Twenty (20) parts by weight of Compound No. 1 was uniformly mixed with 70 parts by weight of xylene by adding 10 parts by weight of Toxanone (trade name, produced by Sanyo Kasei Kogyo K.K.), and dissolved therein to obtain an emulsion.

(4) Preparation of Dust

Five (5) parts by weight of Compound No. 1 was uniformly mixed with 50 parts by weight of talc and 45 parts by weight of kaolin to obtain a dust.

EXAMPLE 4

(1) Activity Test Against Common Cutworm

The respective wettable powders of the compound (I) shown in Table 1 prepared in accordance with Example 2 were diluted to 500 ppm with water containing a surfactant (0.01% and in these respective chemical solutions obtained, soybean leaves were dipped for 30 seconds, respectively. Then, one soybean leaf thus treated was placed in a plastic cup and air-dried.

Ten (10) common cutworms (2nd instar larvae) were freed in the respective cups and a lid was put on the cup. These cups were allowed to stand in a thermostat chamber at 25° C. Two (2) days later, the % mortality was determined by counting the numbers of living and dead insects in the respective cups.

The insecticidal effect of each chemical was evaluated by using 4 ranks depending on the % mortality (A: 100%, B: 99 to 80%, C: 79 to 60% and D: 59% or less).

As a comparative sample, the compound represented by the following formula (VI):

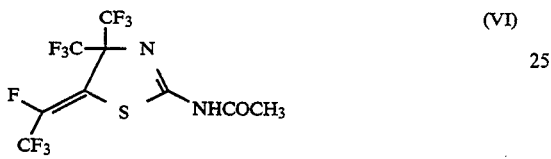

described in Japanese Provisional Patent Publication No. 57371/1983 was used to prepare a comparative preparation in the same manner as mentioned above. The same experiment was carried out for the comparative preparation. The results are shown in Table 2.

TABLE 2

| Compound | Effect |
|---|---|
| 1 | A |
| 2 | A |
| 3 | A |
| 5 | A |
| 6 | A |
| 7 | B |
| 8 | A |
| 13 | B |
| 14 | A |
| 15 | A |
| 21 | A |
| 22 | A |
| 23 | A |
| 26 | A |
| 28 | A |
| 30 | A |
| 32 | A |
| 34 | A |
| 35 | A |
| (VI) | D |

(2) Activity Test Against Diamondback Moth

The respective wettable powders of the compound (I) shown in Table 1 prepared in accordance with Example 2 were diluted to 300 ppm with water containing a surfactant (0.01% and in these respective chemical solutions obtained, cabbage leaves (5 cm×5 cm) were dipped for 30 seconds, respectively. Then, one cabbage leaf thus treated was placed in a plastic cup and air-dried.

Ten (10) diamondback moths (3rd instar larvae) were freed in the respective cups and a lid was put on the cup. These cups were allowed to stand in a thermostat chamber at 25° C. Two (2) days later, the % mortality was determined by counting the numbers of living and dead insects in the respective cups.

The insecticidal effect of each chemical was evaluated by using 4 ranks as described in the above (1) with the comparative sample prepared in the same manner as described in the above (1). The results are shown in Table 3.

TABLE 3

| Compound | Effect |
|---|---|
| 1 | A |
| 2 | A |
| 3 | A |
| 5 | A |
| 6 | A |
| 7 | A |
| 8 | A |
| 9 | A |
| 12 | A |
| 13 | A |
| 14 | A |
| 15 | A |
| 22 | A |
| 23 | A |
| 24 | A |
| 26 | A |
| 30 | A |
| 32 | A |
| 33 | A |
| 34 | A |
| 35 | A |
| (VI) | D |

(3) Activity Test Against Brown Planthopper

The respective wettable powders of the compound (I) shown in Table 1 prepared in accordance with Example 2 were diluted to 300 ppm with water containing a surfactant (0.01% and in the respective chemical solutions were dipped rice young seedlings for 30 seconds. After air-drying, the rice young seedlings were inserted in respective glass cylinders.

Next, ten (10) brown planthoppers (4th instar nymphs) were freed in the respective glass cylinders and a porous lid was put on the cylinder. These cylinders were allowed to stand in a thermostat chamber at 25° C. Four (4) days later, the % mortality was determined by counting the numbers of living and dead insects in the respective cylinders.

The insecticidal effect of each chemical was evaluated by using 4 ranks as described in the above (1) with the comparative sample prepared in the same manner as described in the above (1). The results are shown in Table 4.

TABLE 4

| Compound | Effect |
|---|---|
| 1 | A |
| 3 | A |
| 5 | A |
| 16 | B |
| 21 | A |
| 22 | A |
| 23 | A |
| 28 | B |
| 30 | B |
| (VI) | D |

(4) Activity Test Against Female Adult Two-spotted Spider Mite

The respective wettable powders of the compound (I) shown in Table 2 prepared in accordance with Example 2 were diluted to 300 ppm with water containing a surfactant (0.01% and in these respective chemical solutions obtained, kidney bean leaf strips (diameter: 20 mm) on which 10 female adult two-spotted spider mites were parasitic were dipped for 15 seconds, respectively.

Subsequently, these respective strips were allowed to stand in a thermostat chamber at 25° C. Three (3) days later, the % mortality was determined by counting the numbers of living and dead mites in the respective strips.

The acaricidal effect of each chemical was evaluated by using 4 ranks as described in the above (1) with the comparative sample prepared in the same manner as described in the above (1). The results are shown in Table 5.

TABLE 5

| Compound | Effect |
| --- | --- |
| 1 | A |
| 3 | A |
| 4 | A |
| 5 | A |
| 7 | A |
| 8 | A |
| 12 | B |
| 14 | A |
| 15 | A |
| 16 | A |
| 21 | A |
| 22 | A |
| 23 | A |
| 24 | A |
| 26 | A |
| 27 | A |
| 28 | A |
| 30 | A |
| 32 | A |
| 34 | A |
| 35 | A |
| (VI) | D |

(5) Test of Controlling Effect on Brown Rust (Wheat) (Prevention Effect)

In plastic flowerpots 6 cm in diameter, 10 wheats (variety: Kobushi wheat) were grown per one flowerpot, and to the young plants at 1.5 leaf stage, the chemical solutions obtained by diluting the wettable powders of the compounds (I) shown in Table 1 prepared in accordance with Example 2 to 500 ppm with water containing a surfactant (0.05%) were sprayed in an amount of 20 ml per one flowerpot, respectively.

These wheats thus treated were grown in a glass greenhouse for 2 days, and then a spore suspension of brown rust ($7 \times 10^4$ spores/ml) was sprayed uniformly to the plants to be inoculated thereinto.

Subsequently, the wheats were grown in a glass greenhouse for one week, and the degree of lesion of brown rust appeared on the first leaves was examined.

The effect of each chemical was evaluated by using 6 ranks as compared with the degree of lesion in the non-treated district (0: all area is infected, 1: lesion area is about 60%, 2: lesion area is about 40%, 3: lesion area is about 20%, 4: lesion area is 10% or less and 5: no lesion is observed).

As a comparative sample, the compound represented by the formula (VI) was used to prepare a comparative preparation in the same manner as mentioned above. The same experiment was carried out for the comparative preparation. The results are shown in Table 6.

TABLE 6

| Compound | Effect |
| --- | --- |
| 3 | 4 |
| 5 | 5 |

TABLE 6-continued

| Compound | Effect |
| --- | --- |
| 8 | 4 |
| 26 | 5 |
| (IV) | 0 |
| Non-treated district | 0 |

The novel polyfluorinated thiazoline derivatives of the present invention can be used as agricultural chemicals useful as a chemical for controlling noxious organisms.

We claim:

1. A polyfluorinated thiazoline compound represented by the following formula (I):

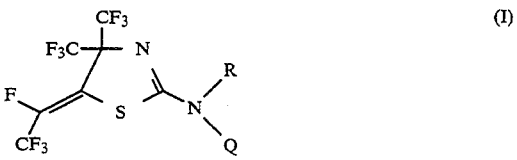

wherein

Q represents a phenyl group; a phenyl group substituted by a halogen atom, a halo-lower alkyl group, a nitro group, a cyano group, a formyl group, a lower alkoxycarbonyl group or a benzoyl group; a pyridyl group; or a pyridyl group substituted by a halogen atom, a halo-lower alkyl group, a nitro group, a cyano group, a formyl group, a lower alkoxycarbonyl group or a benzoyl group; and R represents a hydrogen atom, a lower alkyl group or an acetyl group.

2. The compound according to claim 1, wherein said Q is selected from the group consisting of a phenyl group; a phenyl group substituted by at least one of a halogen atom, a haloalkyl group having 1 to 6 carbon atoms, a nitro group, a cyano group, a formyl group, a alkoxycarbonyl group having 1 to 6 alkoxy carbon atoms and a benzoyl group; a pyridyl group; and a pyridyl group substituted by at least one of a halogen atom, a haloalkyl group having 1 to 6 carbon atoms, a nitro group, a cyano group, a formyl group, a alkoxycarbonyl group having 1 to 6 alkoxy carbon atoms and a benzoyl group.

3. The compound according to claim 1, wherein said Q is selected from the group consisting of a phenyl group; a phenyl group substituted by at least one of a halogen atom, a haloalkyl group having 1 to 4 carbon atoms, a nitro group, a cyano group, a formyl group, a alkoxycarbonyl group having 1 to 4 alkoxy carbon atoms and a benzoyl group; a pyridyl group,; and a pyridyl group substituted by at least one of a halogen atom, a haloalkyl group having 1 to 4 carbon atoms, a nitro group, a cyano group, a formyl group, a alkoxycarbonyl group having 1 to 4 alkoxy carbon atoms and a benzoyl group.

4. The compound according to claim 1, wherein said Q is selected from the group consisting of a phenyl group; a phenyl group substituted by at least one of a chlorine atom, a fluorine atom, a trifluoromethyl group, a nitro group, a cyano group, a formyl group, a methoxycarbonyl group and a benzoyl group; a pyridyl group; and a pyridyl group substituted by at least one of a chlorine atom, a fluorine atom, a trifluoromethyl group, a nitro group, a cyano group, a formyl group, a methoxycarbonyl group and a benzoyl group.

5. The compound according to claim 4, wherein said R is selected from the group consisting of a hydrogen atom, a methyl group and an acetyl group.

6. The compound according to claim 1, wherein the compound is selected from the group consisting of:
2-[(3-chloro-5-trifluoromethyl-2-pyridyl)amino]-4,4-bis(trifluoromethyl)-5-(tetrafluoroethylidene)-2-thiazoline,
2-[(2,6-dichloro-4-trifluoromethylphenyl)amino]-4,4-bis(trifluoromethyl)-5-(tetrafluoroethylidene)-2-thiazoline,
2-[(6-chloro-4-trifluoromethyl-2-pyridyl)amino]-4,4-bis(trifluoromethyl)-5-(tetrafluoroethylidene)-2-thiazoline,
2-[(2-nitro-4-trifluoromethylphenyl)amino]-4,4-bis(trifluoromethyl)-5-(tetrafluoroethylidene)-2-thiazoline,
2-[(2,4-dinitro-6-trifluoromethylphenyl)amino]-4,4-bis(trifluoromethyl)-5-(tetrafluoroethylidene)-2-thiazoline,
2-[(2,6-dinitro-4-trifluoromethylphenyl)amino]-4,4-bis(trifluoromethyl)-5-(tetrafluoroethylidene)-2-thiazoline,
2-[(2,6-dinitro-4-cyanophenyl)amino]-4,4-bis(trifluoromethyl)-5-(tetrafluoroethylidene)-2-thiazoline,
2-[(3-chloro-2,6-dinitro-4-trifluoromethylphenyl)amino]-4,4-bis(trifluoromethyl)-5-tetrafluoroethylidene)-2-thiazoline,
2-[(4-nitro-5-trifluoromethylphenyl)amino]-4,4-bis(trifluoromethyl)-5-(tetrafluoroethylidene)-2-thiazoline,
2-[(3,4-dichloro-2-nitrophenyl)amino]-4,4-bis(trifluoromethyl)-5-(tetrafluoroethylidene)-2-thiazoline,
2-[(4-cyano-2,3,5,6-tetrafluorophenyl)amino]-4,4-bis(trifluoromethyl)-5-(tetrafluoroethylidene)-2-thiazoline,
2-[(2-chloro-4-nitro-5-trifluoromethylphenyl)amino]-4,4-bis(trifluoromethyl)-5-(tetrafluoroethylidene)-2-thiazoline,
2-[(5-fluoro-2-nitro-4-trifluoromethylphenyl)amino]-4,4-bis(trifluoromethyl)-5-(tetrafluoroethylidene)-2-thiazoline,
2-[(2,4-dinitrophenyl)amino]-4,4-bis(trifluoromethyl)-5-(tetrafluoroethylidene)-2-thiazoline,
2-[(4-nitro-2-trifluoromethylphenyl)amino]-4,4-bis(trifluoromethyl)-5-(tetrafluoroethylidene)-2-thiazoline and
2-[(3,5-dinitro-2-pyridyl)amino]-4,4-bis(trifluoromethyl)-5-(tetrafluoroethylidene)-2-thiazoline.

7. The compound according to claim 1, wherein said R is a hydrogen atom.

8. A chemical for controlling noxious organisms which comprises the thiazoline derivative represented by the formula (I) defined in claim 1 as an effective ingredient and a carrier.

* * * * *

UNITED STATES PATENT AND TRADEMARK OFFICE
CERTIFICATE OF CORRECTION

PATENT NO. : 5,369,116
DATED : November 29, 1994
INVENTOR(S) : Tokio OBATA et al It is certified that error appears in the above-indentified patent and that said Letters Patent is hereby corrected as shown below:

Claim 2, column 20, line 39, "a" (fourth occurrence) should read --an--;

line 44, "a" (third occurence) should read --an--.

Claim 3, column 20, line 51, "a" (fourth occurence) should read --an-- line 56, "a" (third occurence) should read --an--.

*Title page, column 1, under "Inventors", lines 2-3, "Yasuhisa Fukuda, Kiyashi Tsutsumiuchi," should read --Yasuhisa Fukuda; Kiyoshi Tsutsumiuchi;--

Signed and Sealed this

Thirtieth Day of May, 1995

Attest:

BRUCE LEHMAN

*Attesting Officer*  *Commissioner of Patents and Trademarks*